(12) United States Patent
Inoue

(10) Patent No.: US 10,512,442 B2
(45) Date of Patent: Dec. 24, 2019

(54) IMAGE PROCESSING APPARATUS, IMAGE PROCESSING METHOD, AND IMAGE PROCESSING SYSTEM

(71) Applicant: CANON KABUSHIKI KAISHA, Tokyo (JP)

(72) Inventor: Noboru Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/134,251

(22) Filed: Sep. 18, 2018

(65) Prior Publication Data

US 2019/0015063 A1 Jan. 17, 2019

Related U.S. Application Data

(63) Continuation of application No. 15/190,541, filed on Jun. 23, 2016, now Pat. No. 10,117,631.

(30) Foreign Application Priority Data

Jun. 30, 2015 (JP) ................................. 2015-132178

(51) Int. Cl.
*G06K 9/00* (2006.01)
*G21K 1/00* (2006.01)
(Continued)

(52) U.S. Cl.
CPC ............ *A61B 6/5282* (2013.01); *A61B 6/467* (2013.01); *A61B 6/5205* (2013.01); *G06T 5/002* (2013.01);
(Continued)

(58) Field of Classification Search
USPC ........ 382/100, 103, 106–107, 128–134, 154, 382/162, 168, 173, 181, 190, 219, 224, 382/232, 254, 274–276, 285–291, 305, 382/312; 600/427; 378/4, 21, 62, 20, 378/154
See application file for complete search history.

(56) References Cited

U.S. PATENT DOCUMENTS

| 8,064,676 B2 * | 11/2011 | Li ............................. A61B 6/00 382/132 |
| 2002/0126800 A1 * | 9/2002 | Matsumoto ............... A61B 6/06 378/154 |

(Continued)

FOREIGN PATENT DOCUMENTS

JP 2015089429 A 5/2015

*Primary Examiner* — Seyed H Azarian
(74) *Attorney, Agent, or Firm* — Canon U.S.A., Inc. IP Division

(57) ABSTRACT

An image processing apparatus includes an acquiring unit and an image processing unit. The acquiring unit acquires a radiographic image acquired by irradiating a radiation on an object and a scattered-ray component contained in the radiographic image, wherein the scattered-ray component originates from a scattered ray which is a radiation scattered in the object. The image processing unit performs an image process on the radiographic image in accordance with an instruction, wherein the image processing unit performs an image process based on a radiographic image acquired by the acquiring unit and a scattered-ray component acquired by the acquiring unit in a case where an instruction to perform the image process is received again.

12 Claims, 9 Drawing Sheets

(51) Int. Cl.
*A61B 6/00* (2006.01)
*G06T 5/00* (2006.01)
(52) U.S. Cl.
CPC ..... *A61B 6/465* (2013.01); *G06T 2207/10116* (2013.01)

(56) References Cited

U.S. PATENT DOCUMENTS

| | | | | |
|---|---|---|---|---|
| 2007/0172028 | A1* | 7/2007 | Tsujii | A61B 6/032 378/20 |
| 2012/0157830 | A1* | 6/2012 | Boyden | A61B 6/482 600/427 |
| 2013/0156158 | A1* | 6/2013 | Noji | A61B 5/08 378/62 |

* cited by examiner

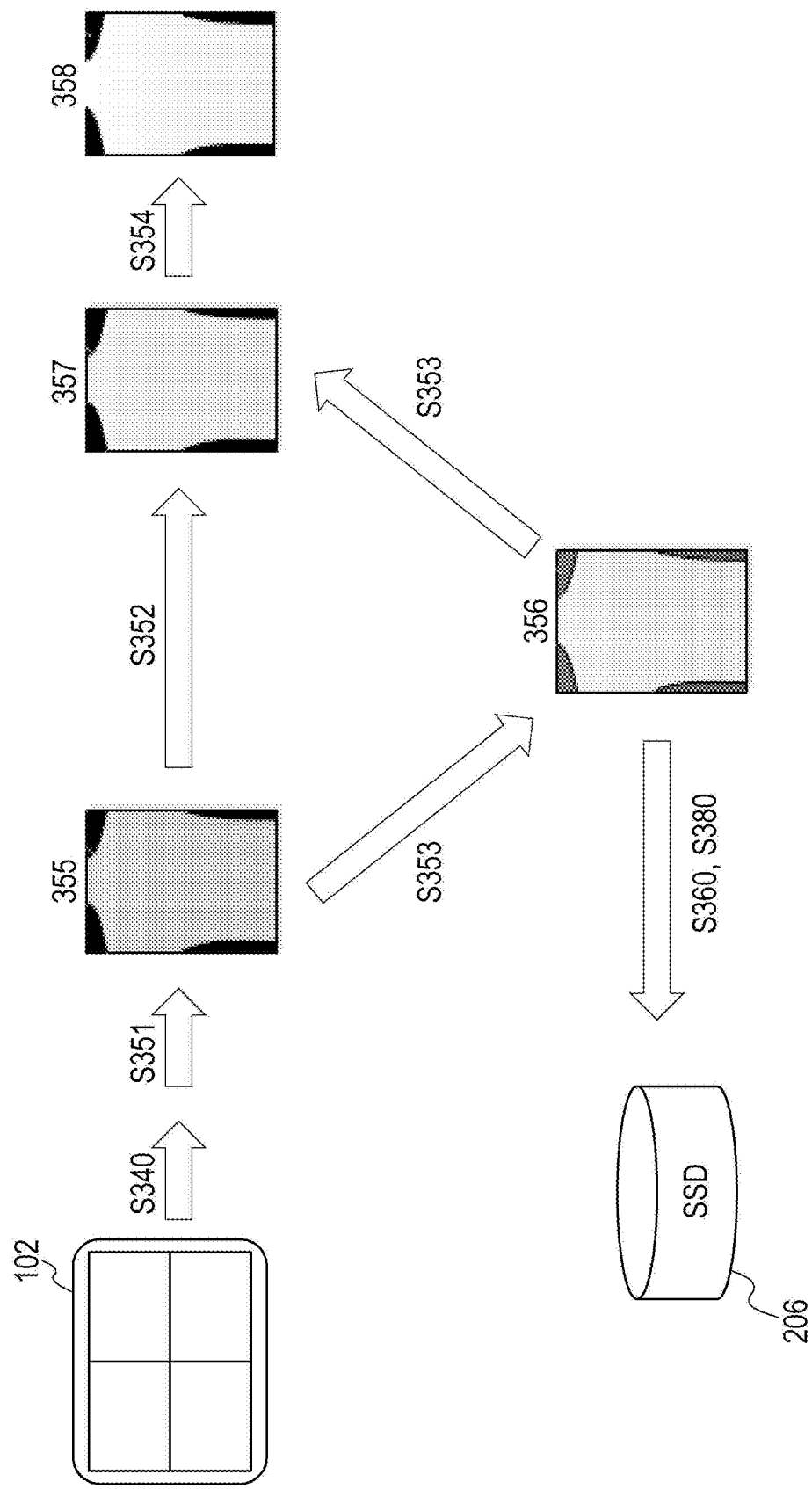

FIG. 5

EXAMINATION INFORMATION

· EXAMINATION ID

· PATIENT INFORMATION

- PATIENT ID

- PATIENT NAME

- AGE
    ⋮

· IMAGING 1

- IMAGING ID

- IMAGING CONDITIONS

· CAPTURING CONDITION

· IRRADIATION CONDITION

· TRANSFER CONDITION

· IMAGE PROCESSING CONDITION

· DISPLAY CONDITION

· OUTPUT CONDITION
          ⋮
  - IMAGE ID

- SCATTERED RAY IMAGE ID
    ⋮
· IMAGING 2
⋮

IMAGE PROCESSING APPARATUS, IMAGE PROCESSING METHOD, AND IMAGE PROCESSING SYSTEM

CROSS-REFERENCE TO RELATED APPLICATIONS

This application is a continuation of U.S. patent application Ser. No. 15/190,541, filed Jun. 23, 2016, which claims the benefit of Japanese Patent Application No. 2015-132178, filed Jun. 30, 2015, all of which are hereby incorporated by reference herein in their entirety.

BACKGROUND OF THE INVENTION

Field of the Invention

The present disclosure herein relates to an image processing apparatus which performs an image process on a radiographic image, an image processing method, and an image processing system.

Description of the Related Art

A radiographic image acquired by irradiating a radiation on an object contains a component originating from a primary radiation which travels straight from a radiation source and a component originating from a scattered ray being a radiation scattered within the object. Such a scattered-ray component may possibly result in reduced contrast of the resulting radiographic image.

In the past, the scattered-ray component contained in a radiographic image has often been reduced by imaging a radiographic image by using a scattered ray reduction grid (hereinafter, called a grid) configured to reduce the amount of a scattered ray reaching a radiation detector for acquiring the radiographic image. In recent years, a method has been proposed which can reduce a scattered-ray component from a radiographic image by performing image processing.

In accordance with some purposes of observation of a radiographic image, a user may perform an image process again with reference to an image generated by performing an image process on a radiographic image. However, the necessity for performing the image process for reducing a scattered-ray component every time an image process is performed may possibly increase the processing time.

SUMMARY OF THE INVENTION

According to some embodiments of the present invention, an image processing apparatus includes an acquiring unit configured to acquire a radiographic image acquired by irradiating a radiation on an object and a scattered-ray component contained in the radiographic image, wherein the scattered-ray component originates from a scattered ray which is a radiation scattered in the object, and an image processing unit configured to perform an image process on the radiographic image in accordance with an instruction, wherein the image processing unit is configured to perform an image process based on a radiographic image acquired by the acquiring unit and a scattered-ray component acquired by the acquiring unit in a case where an instruction to perform the image process is received again.

Further features of the present invention will become apparent from the following description of exemplary embodiments with reference to the attached drawings.

BRIEF DESCRIPTION OF THE DRAWINGS

FIGS. 3A to 3C illustrate workflows for using an image processing apparatus according to an embodiment of the present invention.

FIG. 5 illustrates a configuration of a file generated by an image processing apparatus according to an embodiment of the present invention.

DESCRIPTION OF THE EMBODIMENTS

Figure 1:
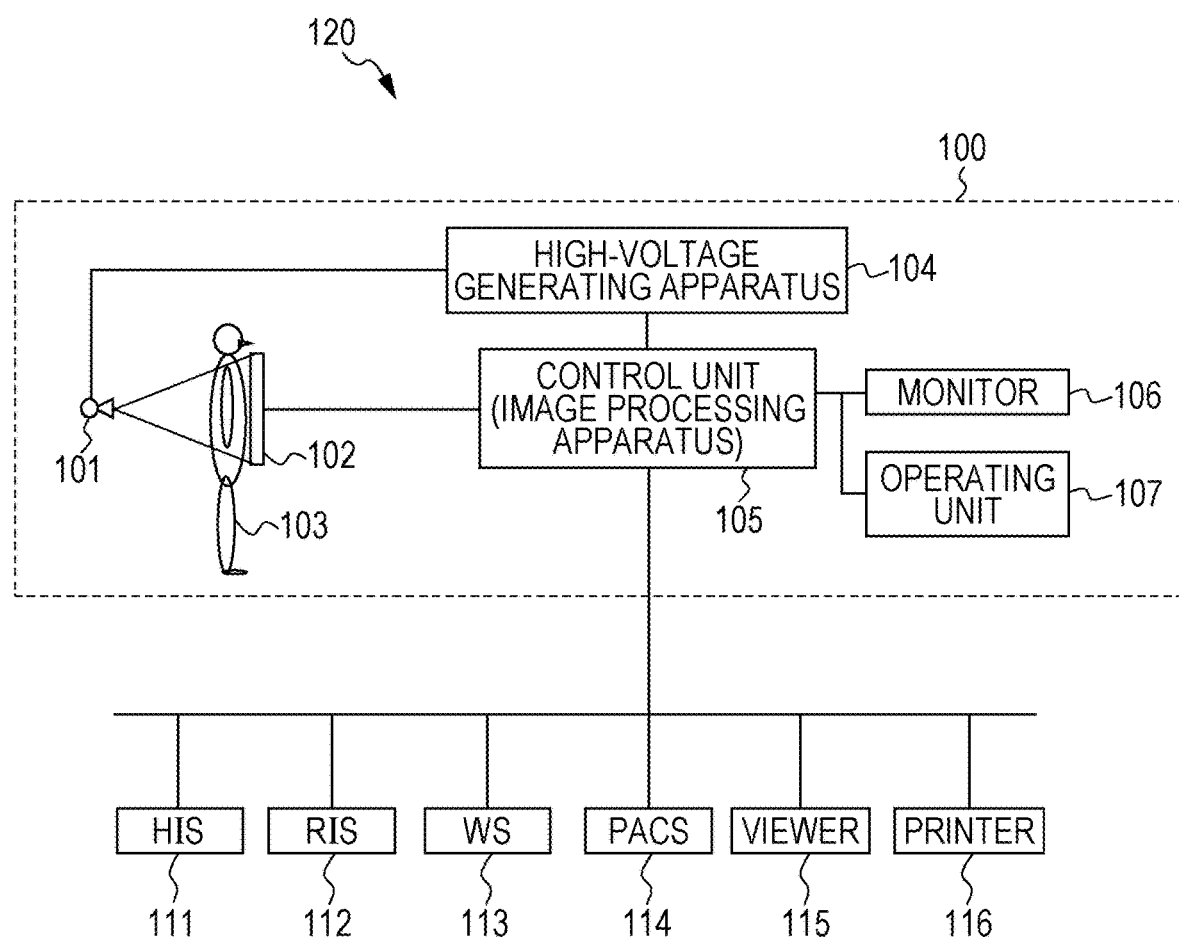
FIG. 1 illustrates a configuration of an information system including an image processing apparatus according to an embodiment of the present invention.

An image processing apparatus according to an embodiment of the present invention and an information system 120 including a radiography system 100 will be described with reference to FIG. 1. An image processing apparatus according to an embodiment corresponds to a control unit 105 included in the radiography system 100. Hereinafter, the control unit 105 will sometimes be called an image processing apparatus 105 from the perspective of description regarding an image process according to the present invention. The information system 120 is configured to manage information before and after imaging a radiographic image and may include, for example, Hospital Information System (HIS) 111, a Radiography Information System (RIS) 112, a Work Station (WS) 113, a Picture Archiving and Communication System (PACS) 114, a Viewer 115 and a Printer 116. The HIS 111 is a system configured to generally manage patient information and information regarding a diagnosis including a radiographic examination. The RIS 112 is a system configured to manage radiographing orders. The WS 113 is an image processing terminal and is configured to perform an image process on a radiographic image captured in the radiography system 100. The WS may be replaced by one or more computers in which a software program having the same function as described above is installed. The PACS 114 is a database system configured to hold images radiographed within the information system 120 or acquired by other medical image photographing apparatuses. The PACS 114 has a storage unit (not illustrated) configured to store a medical image and an imaging condition for the medical image and attached information such as patient information and a controller (not illustrated) configured to manage information stored in the storage unit. The Viewer 115 is a terminal for diagnostic imaging and is configured to read out an image stored in the PACS 114, for example, and display it for diagnosis. The Printer 116 may be a film printer, for example, and may output an image stored in the PACS 114, for example, onto a film.

The radiography system 100 according to an embodiment applies an X-ray as a radiation. The radiography system 100 has an X-ray source 101 which is an example of a radiation generating apparatus, a flat panel detector (FPD) 102, and a control unit 105. These components are connected through a cable or a communication system. The control unit 105 attaches an imaging condition for photographing and patient information to a radiographic image acquired as a result of the photographing. For example, information may be attached under DICOM (Digital Imaging and Communications in Medicine) standards to generate a DICOM image file containing data of a radiographic image, patient information, and information regarding an imaging condition and so on. The control unit 105 transmits the image to the WS 113 and the PACS 114. An order for the radiographing may be transmitted from the RIS 112 to the control unit 105. The control unit 105 reads out an imaging condition from a storage unit (not illustrated) in accordance with input information from the RIS 112.

The X-ray source 101 may be an X-ray tube or any other arbitrary radiation source for acquiring a medical image or other images. A high-voltage generating unit 104 applies high-voltage pulses to the X-ray source 101 in response to a user's press of an exposure switch to expose a region having an object 103 to an X-ray from the X-ray source 101. The X-ray having passed through or around the object 103 enters to the FPD 102 being an X-ray detector. The FPD 102 is controlled by the control unit 105 and is configured to convert the entered X-ray to an electric signal and then transmit it as a digital image to the control unit 105. For example, in the FPD 102, a phosphor (not illustrated) may convert an entered X-ray to visible light, a photodiode (not illustrated) detects the visible light, and an A/D converter (not illustrated) converts it to an electric signal. Alternatively, an amorphous selenium (not illustrated) in the FPD 102 may convert an X-ray to an electric signal. A pixel value of a radiographic image may be acquired from an output from a radiation detecting element (not illustrated) included in the FPD 102. The radiation detecting element (not illustrated) may include a phosphor (not illustrated) and a photodiode (not illustrated), for example. In another example, the radiation detecting element may include an amorphous selenium (not illustrated).

The digital image undergoes image processing in the control unit 105 and the WS 113 and is stored in the PACS 114, for example. The components of the information system 120 may be mutually connected through a bus or any other communication system and may be located remotely from each other.

Figure 2:
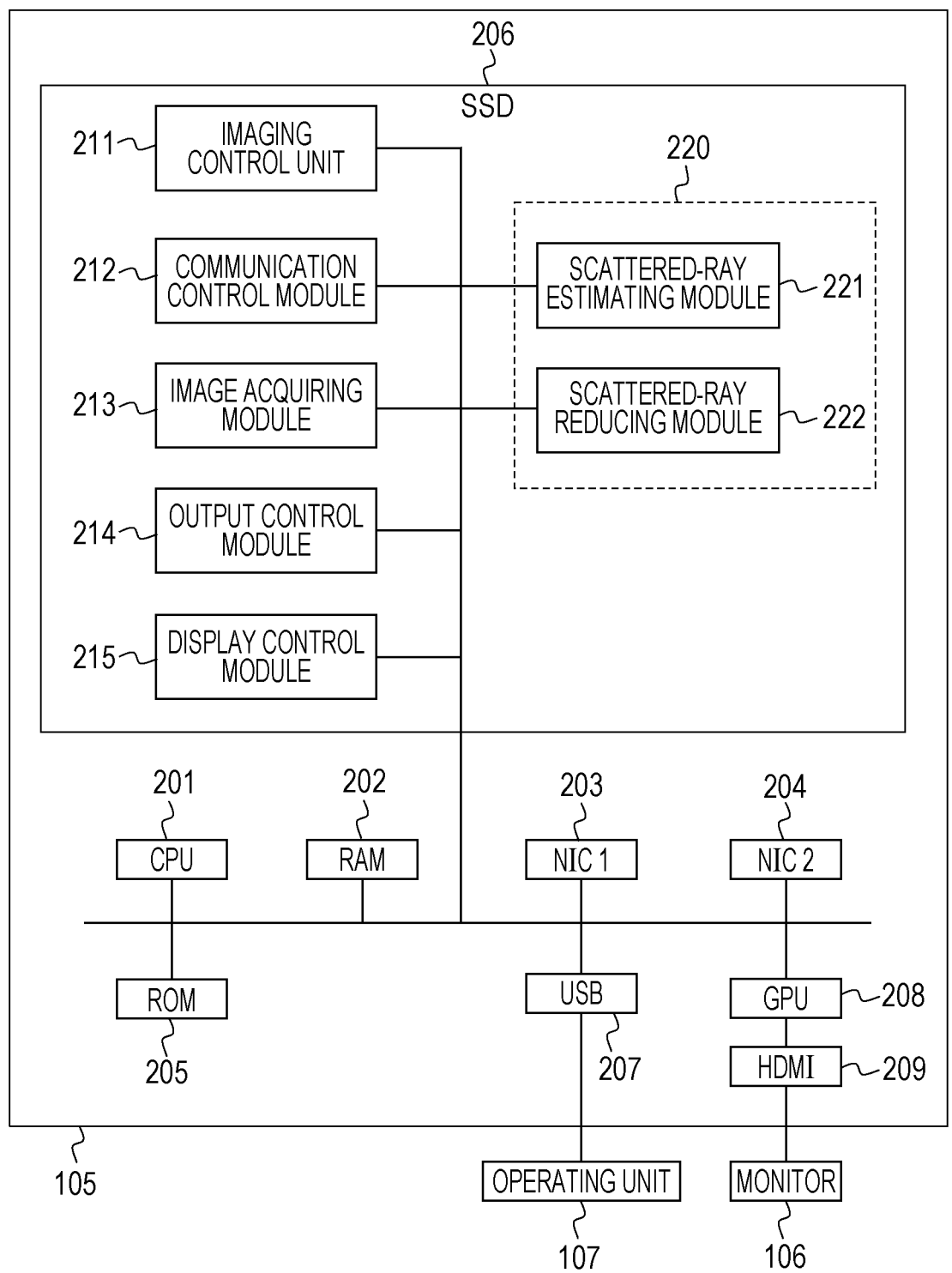
FIG. 2 illustrates a configuration of an image processing apparatus according to an embodiment of the present invention.

Next, with reference to FIG. 2, a configuration of an image processing apparatus according to an embodiment of the present invention will be described in detail. The image processing apparatus according to an embodiment of the present invention is the control unit 105 connected to the information system 120 and the radiography system 100 and may be implemented by one or more computers. The computer or computers implementing the control unit 105 has a Central Processing Unit (CPU) 201 being a main control unit, a Random Access Memory (RAM) 202 being a storage unit, a Read Only Memory (ROM) 205, a Solid State Drive (SSD) 206, a Graphics Processing Unit (GPU) 208 being a graphics control unit, Network Interface Cards (NICs) 203 and 204 being communication units, a Universal Serial Bus (USB) 207 being a connecting portion, and an HDMI (registered trademark) (High Definition Multimedia Interface) 209, all of which are communicably connected via an internal bus. The CPU 201 is a control circuit configured to control the control unit 105 and the components connected thereto in a unified manner. The RAM 202 is a memory configured to store programs for executing processes in the control unit 105 and the components connected thereto and parameters to be used for image processes. Instructions contained in a program decompressed in the RAM 202 are executed successively by the CPU 201 so that an image process, which will be described below, can be executed. For example, a first NIC 203 being a communication unit may connect to an access point in facility where a radiographing is to be performed. A second NIC 204 may connect to an access point for relating a communication within the information system 120. The SSD 206 is configured to store programs as described above, a radiographic image acquired by imaging, attached information, and parameters. The USB 207 connects to an operating unit 107. The GPU 208 is an image processing unit and is configured to execute an image process under control of the CPU 201. An image resulting from an image process is output to a monitor 106 through the HDMI (registered trademark) 209 for display. The monitor 106 may be a touch panel monitor, and the operating unit 107 may be a stylus pen.

Programs stored in the SSD 206 may be an imaging control module 211, a communication control module 212, an image acquiring module 213, an output control module 214, a display control module 215, an image processing module 220, and a scattered-ray estimating module 221 and a scattered-ray reducing module 222 included in the image processing module 220. Each of the modules is executed by the CPU 201 or the GPU 208 to function.

The imaging control module 211 is a program causing the CPU 201 to control a radiographing operation through execution of an image process and output of data of an image having undergone the image process in a unified manner according to this embodiment. The imaging control module 211 may acquire information regarding a user, for example. The imaging control module 211 may designate an imaging condition based on an operation input and transmit a signal for requesting the state of the FPD 102. The imaging control module 211 determines the next process in accordance with a processing result output from a module and causes the corresponding module to perform the process. The imaging control module 211 pre-holds one or more conditions of imaging conditions input from the RIS 112 in the RAM 202 or the SSD 206. For example, the conditions may include an X-ray tube voltage, an X-ray tube current, an irradiation time, and an object region. These conditions may be used to control the image processing module 220.

The communication control module 212 controls communication performed by the first NIC 203 and the second NIC 204. The communication control module 212 causes a communication unit (not illustrated) to transmit a signal for shifting the FPD 102 to an imageable state in accordance with control from the imaging control module 211 or in response to an input from the operating unit 107. The communication control module 212 also causes a communication unit (not illustrated) to transmit a signal for shifting the high-voltage generating unit 104 to a state that high voltage pulses can be generated for the X-ray source 101 in accordance with control from the imaging control module 211 or in response to an input from the operating unit 107.

The image acquiring module 213 controls a process for acquiring an image subjecting to an image process according to an embodiment of the present invention. For example, the image acquiring module 213 causes the NIC 203 to receive a radiographic image captured by the FPD 102. In processing for receiving a radiographic image, a reduced image of a radiographic image having a smaller data amount may be received first, and data of the radiographic image excluding the data of the reduced image may then be received to complete the processing for receiving the radiographic image. Such a reduced image may be acquired by using output signals selectively read out from partial pixels of even-numbered columns, for example, of a plurality of radiation detecting elements included in the FPD 102 and configured to give pixel values of a radiographic image. Alternatively, signals may be read out from some pixels collectively. The read out image may be divided into a plurality of sub-regions, and a reduced image thereof may be generated by using a representative value of the sub-regions. The image acquiring module 213 causes the NIC 203 to receive a radiographic image stored in the PACS 114 or another storage unit on the network. The image acquiring module 213 further reads out a radiographic image stored in the SSD 206 in the image processing apparatus 105, the PACS 114 or another storage unit (not illustrated) in accordance with an operation input.

The image processing module 220 performs an image process on the radiographic image acquired by the image acquiring module 213. The image processing module 220 may include, for example, the scattered-ray estimating module 221 and the scattered-ray reducing module 222. Image processes to be performed by the image processing module 220 may include publicly known image processes excluding processes to be performed by the scattered-ray estimating module 221 and the scattered-ray reducing module 222. The image processing module 220 may be implemented by the CPU 201 or the GPU 208. Specific details of the image processes will be described below.

The output control module 214 is configured to control output of data of a processed image being an image having undergone an image process performed by the image processing module 220 and a re-processed image being an image having undergone an image process again. The output control module 214 is also configured to control output of data of a scattered-ray component estimated by the image processing module 220. For example, the output control module 214 outputs data of a processed image to the monitor 106 so that the monitor 106 can be caused to display the processed image. For example, the output control module 214 may output data of a processed image to the PACS 114 or the Printer 116 through the NIC 204. Thus, the processed image can be saved in the PACS 114, and the processed image can be output onto a film by the Printer 116. The data of the scattered-ray component are output to a non-volatile memory such as the SSD 206. Thus, the data of the scattered-ray component are saved in the SSD 206. The output control module 214 may output and store data of a processed image in another storage unit (not illustrated) inside or outside the control unit 105. Based on DICOM standards, data of a processed image may be output together with various information. An image-generating unit called a modality is configured to image a patient to generate a medical image. In the information system 120 according to an embodiment of the present invention, the radiography system 100 having the X-ray source 101 and the FPD 102 corresponds to the modality. In this case, DX indicative of Digital Radiography is attached as a Modality tag (0008, 0060). For movie capturing, RF indicative of Radio Fluoroscopy is attached thereto. When data as described above are saved in the PACS 114, 1.2.840.10008.5.1.4.1.1.1.1 indicative of a combination of Digital X-ray Image of Object and Storage of Service are attached as a SOP Class UID (0008,0016) tag being a tag designating a Pair of Service and Object. Information for identifying the scattered-ray component image may further be included in the DICOM tag. The information for identifying a scattered-ray component image may be an ID assigned to the scattered-ray component image or a path to a location where the scattered-ray component image is stored. A file having the information for identifying the scattered-ray component image may be saved in association with the radiographic image, instead of the inclusion in the DICOM tag.

The display control module 215 is configured to control a content to be displayed on the monitor 106. For example, under control of the imaging control module 211, a screen for setting a condition for a radiographic operation may be displayed on the monitor 106. Based on user information acquired by the imaging control module 211, a function that the user is permitted to use is displayed in an operable manner on the monitor 106. Under control of the imaging control module 211, patient information, information regarding an imaging condition and information describing the state of the FPD 102 are displayed on the monitor 106. Furthermore, under control of the control module 211 and the image processing module 220, a screen notifying some information to a user is displayed on the monitor 106.

According to another embodiment, the display control for displaying a processed image or a re-processed image on the monitor 106 may be performed by the display control module 215 instead of the output control module 214.

It should be understood that some or all of the components of the control unit 105 are not fixed to the control unit 105 but may be implemented as an image processing system included in the information system 120. For example, an image processing apparatus configured to execute image processing programs having the image acquiring module 213, output control module 214, and image processing module 220 may be provided separately from the control unit 105 which executes the imaging control module 211. Alternatively, the WS 113 may be some or all of the modules. The PACS 114 may have some or all of the modules. The FPD 102 may have a field-programmable gate array (FPGA) in which the image processing module 220 is programmed, and the FPD 102 may transmit an image having undergone an image process performed by the image processing module 220 to the control unit 105. The components of the control unit 105 may be included in a different apparatus in an overlapped manner, and the apparatuses to perform processing may be selected in accordance with a user's instruction. Furthermore, the components may be implemented by a work station, a server, and a storage device, all of which are connected over a network, and an image process according to an embodiment of the present invention may be performed in communication with those devices.

Next, with reference to FIGS. 3A to 3C and FIGS. 6A and 6B, the flow including imaging, image processing and output operations to be performed on a radiographic image by using the radiography system 100 and the information system 120 will be described. The following description assumes that the entity implementing processes of the modules in the following processing is the CPU 201 or the GPU 208 otherwise specified.

In step S310, information regarding a user who performs an X-ray imaging operation is acquired. For example, an ID is given that is information by which a user within facilities for performing X-ray imaging is identified. The display control module 215 causes the monitor 106 to display a screen prompting input of identification information of a user in accordance with an operation input. The user may input the given ID through the operating unit 107, and the imaging control module 211 acquires user information based on the user ID. The term "user information" refers to information regarding a name of a user and a function that the user is permitted to use.

Figure 6A:
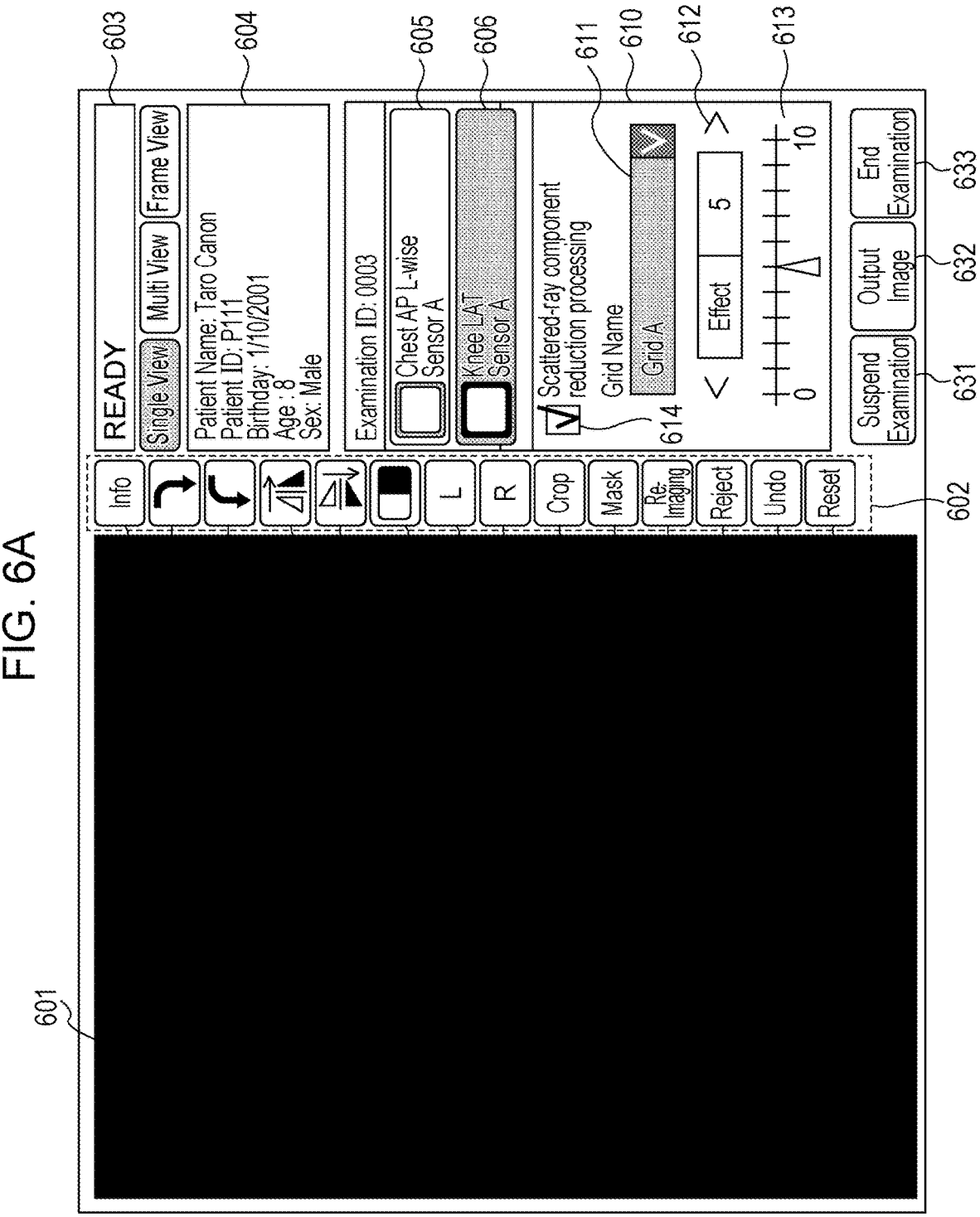
FIGS. 6A and 6B illustrate example screens to be displayed on a monitor by an image processing apparatus according to an embodiment of the present invention.

After the user information is acquired in step S310, the display control module 215 in step S320 displays an examination screen on the monitor 106. Based on the user information acquired by the imaging control module 211, the function that the user is permitted to use is only displayed in an operable manner. Here, the term "examination" refers to a process including acquiring an X-ray image, performing a requested image process on the X-ray image and ending the operation. For example, a screen as illustrated in FIG. 6A is displayed.

Next, an examination screen will be described with reference to FIG. 6A. A region 601 displays an X-ray image acquired by the image acquiring module 213.

A region 602 displays an icon for performing an operation input relating to an image process or imaging.

A region 603 displays whether the FPD 102 is ready for radiographing or not. The imaging control module 211 controls the display control module 215 based on a received signal indicating the state of the FPD 102 and displays "READY" if the FPD 102 is ready for X-ray imaging. If the FPD 102 has a state not suitable for X-ray imaging, "NOT READY" is displayed.

A region 605 and a region 606 display imaging conditions for X-ray imaging based on an X-ray imaging order input from the RIS 112. Here, based on user information, an order for imaging to be performed by the user may only be displayed among X-ray imaging orders input from the RIS 112. In this case, the region 606 may display information regarding imaging conditions for different imaging operations to be performed on an identical patient or an order relating to another imaging operation to be performed by the user. Imaging conditions here may include radiographing conditions, an irradiation condition, a transfer condition, an image processing condition, a display condition, and an output condition. The radiographing conditions may be settings relating to a gain of the FPD 102, binning processing, and a storage time. The irradiation condition is settings relating to an X-ray tube voltage, an X-ray tube current, and an X-ray irradiation time of the X-ray source 101. The transfer condition is a setting for transferring a captured X-ray image from the FPD 102 to the control unit 105. The image processing condition is a setting designating whether an image process is to be performed or not and how much the process is to be performed. The display condition is a setting for displaying a content fitted to an imaging scheme to be used on the monitor 106. The output condition is a setting relating to an output destination of a captured radiographic image. Based on these imaging conditions, an imaging protocol is determined. The protocol may be automatically selected based on the imaging conditions or based on an operation input. When a plurality of orders are displayed as in the region 605 and the region 606, an order being a state before an examination, an order being a state of the examination in progress, an order of a state that the examination ends, an order that an examination is started but is interrupted are displayed such that they can be distinguished. For example, the colors of the order display regions may change in accordance their states.

A region 604 displays patient information at a selected order, that is, the order displayed in the region 605 among the plurality of displayed orders. The patient information is information regarding patient's name, ID, sex and so on.

A region 610 displays details relating to a scattered-ray component reduction process. Regions 611 to 622, details of which will be described below, are usable for defining settings relating to a scattered-ray component reduction process. A region 614 is a checkbox for setting whether a scattered-ray component reduction process is to be performed or not. These settings may be changed before and after an imaging operation.

A region 631 is usable for performing an operation input for interrupting an examination at a selected order. A region 632 is displayed in the region 601 and is usable for performing an operation input for outputting an X-ray image captured in step S330 or an image acquired by performing an image process on the X-ray image. For example, such an image may be output to and be stored in the SSD 206. This can be performed during an examination. A region 633 is usable for performing an operation input for finishing an examination. When an examination ends, an image displayed in the region 601 is output. For example, the image may be output to and be stored in the SSD 206. Details of processing relating to the image output will be described below.

In step S330, an X-ray image is captured in accordance with a user's operation input. The imaging is performed based on set imaging conditions. The user may select an order for imaging from orders displayed on the monitor 106. For example, the region 605 may be selected by using the operating unit 107. The imaging control module 211 shifts the high-voltage generating unit 104 to a state that it is ready for generation of high-voltage pulses based on the imaging conditions at the selected order and shifts the FPD 102 to an imaging-ready state. When the FPD 102 is shifted to a storage state allowing imaging of an X-ray image, the fact is displayed on the monitor 106. When a user identifies the displayed "Ready" indicating that the shift to the storage state is completed and that X-ray imaging is ready, the user may press an exposure button (not illustrated) to expose the object 103 to the X-ray. The X-ray having transmitted through the object 103 is detected by the FPD 102. The X-ray reaching the FPD 102 is converted to an electric signal so that data of the corresponding X-ray image can be generated. A grid may also be used for imaging.

A radiographic image captured by irradiating a radiation from the X-ray source 101 is an input image subjecting to an image process according to this embodiment. In another example, a reduced image having a smaller data amount may be acquired and be handled as an input image subjecting to an image process according to this embodiment. Thus, an image process subsequent to data transmission from the FPD 102 can be performed quickly. Because a scattered-ray component mainly contains a low frequency component, estimation from such a reduced image may have a smaller influence on the accuracy of estimation of the scattered-ray component.

Figure 6B:
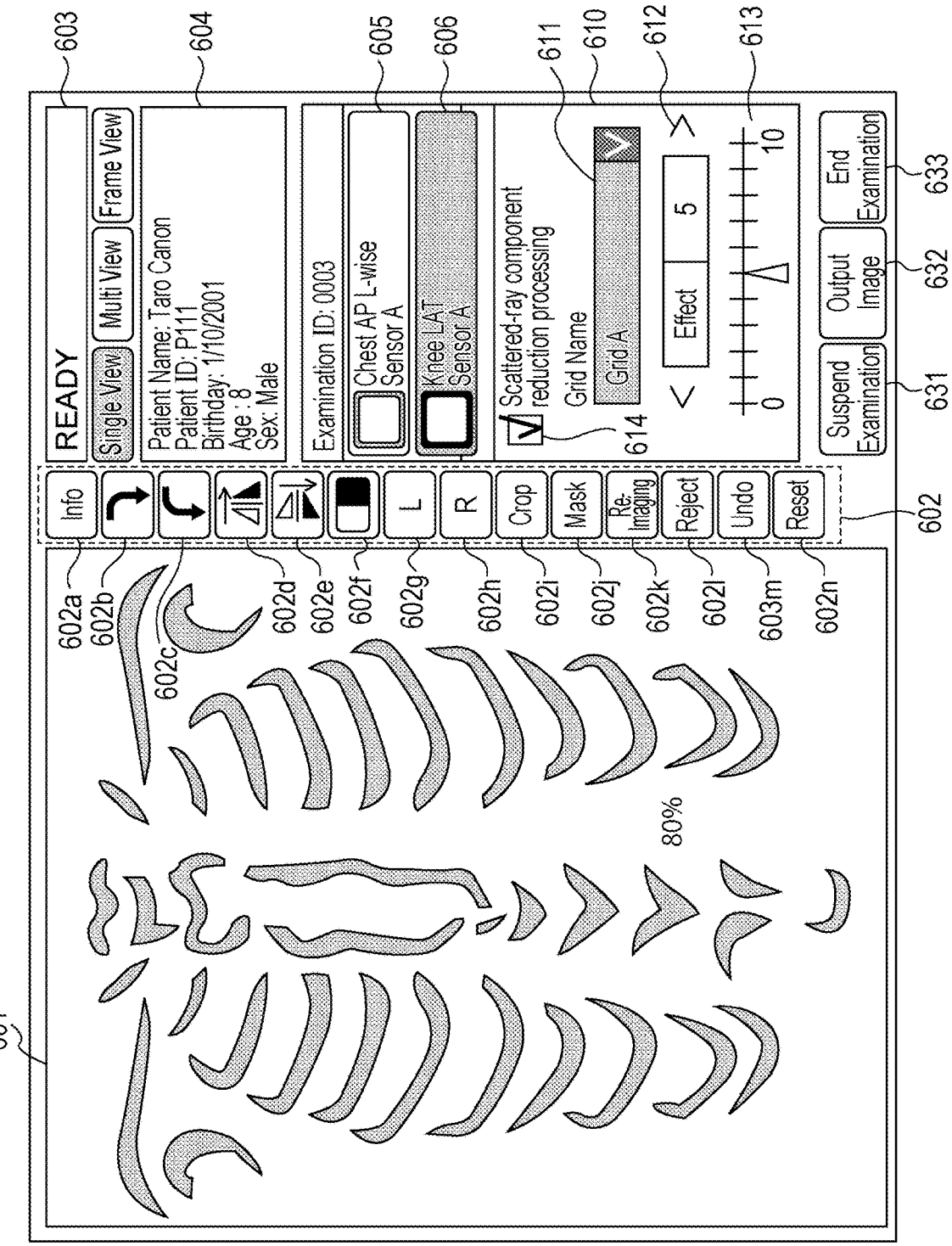

In step S340, the control unit 105 receives the data of the X-ray image from the FPD 102 by using the image acquiring module 213 and obtains the X-ray image. The X-ray image is stored in the RAM 202 once and then is saved in the SSD 206. The obtained X-ray image is displayed in the region 601 by the display control module 215. For example, a screen as illustrated in FIG. 6B may be displayed on the monitor 106.

In step S350, the image processing module 220 performs an image process on the X-ray image. A flow for performing an image process will be described with reference to FIG. 3B and FIG. 3C. The patient information and imaging conditions acquired by the imaging control module 211 are used as required for the image process in step S350.

In step S351, the image processing module 220 performs a first image quality adjustment on the X-ray image acquired in step S340. For example, the adjustment may include a process for correcting variations of characteristics of a phosphor (not illustrated) of the FPD 102, a process for correcting a pixel having a lattice defect, and a process for correcting blurring originating from the FPD 102. In a case where imaging is performed by using a grid in step S310, a stripe pattern originating from the grid may possibly superimposed on the acquired X-ray image. Therefore, if information describing that a grid has been used for imaging in step S330 is acquired, the image processing module 220 performs an image process for reducing the stripe pattern originating from the grid. An image 355 acquired in step S351 is analyzed, and a histogram representing the magnitudes and frequencies of signals of pixels is generated.

In step S352, the image processing module 220 performs a second image quality adjustment on the image 355 acquired by performing the first image quality adjustment in step S351. For example, the sharpness of the image may be adjusted. This may be executed by performing a publicly known sharpening filter such as a Laplacian filter. A process for reducing noise may also be performed. This may be executed by using a publicly known noise reduction filter such as a low pass filter, ε filter, a bilateral filter, and nl-means.

In step S353, the scattered-ray estimating module 221 estimates a scattered-ray component contained in the X-ray image based on the image having undergone the first image quality adjustment in step S351. Then, the scattered-ray reducing module 222 reduces the scattered-ray component from the image having undergone the second image quality adjustment in step S352.

The estimation of a scattered X-ray component may be executed by the following method, for example. It is assumed that an X-ray image being an input image in the estimation process is M, a primary X-ray component is P, and a scattered X-ray component is S, and that a sum total of P and S coincides M. In this case, the following Expression (1) can be satisfied.

$$M = P + S \quad (1)$$

Expressing an approximation representing the scattered X-ray component S by using the primary X-ray component P, Expression (1) may be solved about P to estimate the scattered-ray component. For example, an approximation expressing the scattered X-ray component S by using the primary X-ray component P may be Expression (2).

$$S = -P \ln P^*(G_1 + G_2) \quad (2)$$

Here, each of $G_1$ and $G_2$ is a Gaussian function for modeling the spread of a scattered ray. * is a convolution operator.

From the primary X-ray component P acquired from Expressions (1) and (2), the scattered X-ray component S can be estimated.

The reduction of the scattered X-ray component can be adjusted to a degree requested by a user. For example, as an criterion for the effect of the scattered X-ray reduction in the region 611, the type of a grid may be input. The transmittance for a primary X-ray and the transmittance for a scattered X-ray of each grid may be obtained with reference to JIS standards, for example. An image M' after the scattered X-ray component is reduced can be expressed by Expression (3).

$$M' = \alpha P + \beta S \quad (3)$$

where the acquired transmittance of a primary X-ray is $\alpha$ and the transmittance of a scattered X-ray is $\beta$.

A region 612 has an "Effect" field displaying the degree of reduction on a scale of numerical values 1 to 10. The numerical value may be directly input by an operator. A region 613 represents the degree of reduction on a number line. An icon indicating the effect is displayed on the number line, and the degree of reduction can be operated by a user through the icon. The adjustment methods displayed in the region 611 to the region 613 may be used by a user separately from each other or may be used in combination. In a case where the degree of scattered-ray reduction is adjusted, the value of factor $\beta$ in Expression (3) is adjusted.

In step S354, the image processing module 220 performs the second image quality adjustment in step S352 and performs third image quality adjustment on an image 357 acquired by reducing the scattered X-ray component 356 estimated in step S353. For example, based on the histogram of pixel values acquired in step S351 and information describing an imaged region, a process for adjusting contrast, a dynamic-range compression process, and a frequency emphasis process and so on may be performed.

The scattered X-ray component may be reduced by the process performed in step S350 so that a processed image 358 having undergone image processes can be acquired. The images generated in the middle of the processing, such as the image 355 to image 357, may be stored in the RAM 202 until the examination ends. This can reduce the time required for the processing performed every time a user changes a parameter of any one of the image processes. During the processing in step S350, the display control module 215 may update the screen displayed in the region 601 every time an image process is performed.

In step S360, the output control module 214 and the display control module 215 output the processed image 358. The processed image 358 and information associated with the processed image 358 are displayed on the monitor 106 under control of the output control module 214 and the display control module 215. The output control module 214 outputs the processed image to the PACS 114 and the Printer 116 through the NIC 204. Thus, the processed image can be saved in the PACS 114, and the processed image can be output onto a film, for example, by the Printer 116. The output control module 214 associates information based on DICOM standards with the image in step S350 and outputs the information together with the image. The output control module 214 outputs to and stores in a non-volatile memory such as the SSD 206 the data of the processed image 358 and the scattered X-ray component 356. In this case, information for identifying the data of the scattered X-ray component 356 used for generating the processed image is attached in advance to the processed image 358. For example, the image processing module 220 gives a scattered-ray image ID when data of a scattered X-ray component is generated. The corresponding scattered-ray image ID is attached to the processed image 358. For example, under DICOM standards, a setting may be defined such that a private tag can be used for the scattered-ray image ID. The output control module 214 associates a scattered-ray image ID being information for identifying data of the scattered X-ray component 356 with information regarding the processed image 358 under DICOM standards and stores the scattered-ray image ID in the private tag. An image of the scattered X-ray component 356 may be inserted to a DICOM file of the processed image 358. For example, under DICOM standards, a plurality of images as described above may be output in a multi frame format. The association with information is not limited to be based on DICOM standards. For example, information as illustrated in FIG. 5 may be attached in an identifiable manner. In addition to the scattered-ray image ID, for example, information by which a parameter indicative of the degree of reduction of a scattered X-ray component and an algorithm for estimating a scattered X-ray component can be identified may also be attached. The information by which the algorithm can be identified is version information of a software program for implementing an image process according to the present invention. The software program may be executed by a module included in the SSD 206, for example. In a case where a plurality of algorithms are available and selectable by a user, information by which the algorithm used for estimating the scattered X-ray component can be identified may be attached. The output control module 214 may attach a parameter for the image process performed in step S350 and information by which data of the scattered X-ray component 356 can be identified to the X-ray image acquired by the image acquiring module 213 for output.

Under some imaging conditions or user's settings, the scattered-ray component reduction process in step S353 may not be performed. In this case, the processed image 358 acquired by performing an image process in step S350 is an image without reducing a scattered X-ray component therein. Because the estimation of a scattered X-ray component is not performed in step S353, the output control module 214 does not perform the process for attaching the scattered-ray image ID to the processed image 358 in step S350.

After the processing in step S360 completes, it is ready in step S370 for receiving an instruction for performing an image process again. In response to an operation input for ending the examination without receiving an instruction for performing an image process again, the examination ends. The display control module 215 controls so as not to display an imaging order of the examination and displays the next imaging order. In a case where no imaging order is present, the display control module 215 may display a screen for notifying a user of that no next imaging order is present.

If an instruction for performing an image process again is given in step S370, the image process is performed in step S380. A re-processed image being an image having undergone the instructed the image process is output in step S390. The re-processed image is displayed on the monitor 106 under control of the display control module 215 and is output to the SSD 206. Because the output processing in step S380 is the same as the processing in step S360, the detail description will be omitted.

Other examples of re-processing may include observing and performing an image process on an X-ray image captured in the past again. In this case, user information is acquired in step S310 in the same manner as described above, and an examination screen is displayed in step S320. Because imaging in step S330 is not necessary, the processing moves to step S340. In step S340, the image acquiring module 213 reads out a desired X-ray image from the SSD 206 or the PACS 114 in response to a user's operation input. The acquired X-ray image is displayed in the region 601 under control of the display control module 215. Without processing in step S350 and step S360, a state is obtained in step S370 in which an instruction to perform an image process again is acceptable. If an instruction to perform an image process again is not given, the processing moves to step S3100 where the examination ends in response to an operation input for ending the examination. If an instruction to perform an image process again is given in step S370, the processing moves to step S380.

The instruction to perform an image process again may be started in response to an operation input performed on an image process icon displayed in the region 602 in FIG. 6B through the operating unit 107, for example. An icon 602a is usable for selecting a process for displaying information describing a condition relating to an imaging operation to be performed. Icons 602b to 602j are usable for selecting respective image processes. An icon 602k is usable for selecting a process for performing a re-imaging operation. An icon 602l is usable for selecting a process for inhibiting use for a diagnosis of an X-ray image acquired by an imaging operation in a case where a user determines the X-ray image as an image not suitable for a diagnosis, that is, a rejected image. When an operator performs an operation input for selecting the icon 602l, the CPU 201 executes the display control module 215 to display a screen prompting to input the reason for the determination of a rejected image.

An instruction to perform an image process again may be started in response to a change of a detail of the scattered-ray component reduction process displayed in the region 610 through the operating unit 107.

If the image process instructed to perform again ends, or if an image process is not performed again, the image processing apparatus 105 has a standby state in which an operation input to end the examination in step S3100 is acceptable or in which an instruction to perform an image process again in step S370 is acceptable. If no operation input to end the examination is given in step S3100, the processing returns to step S370. If an instruction to perform an image process again is received in step S370, the processing in steps S380 and S390 is performed in the same manner as described above and then moves to step S3100. Until the operation input to end the examination is received in step S3100, the processing above may be repeated a plurality of number of times.

Figure 4:
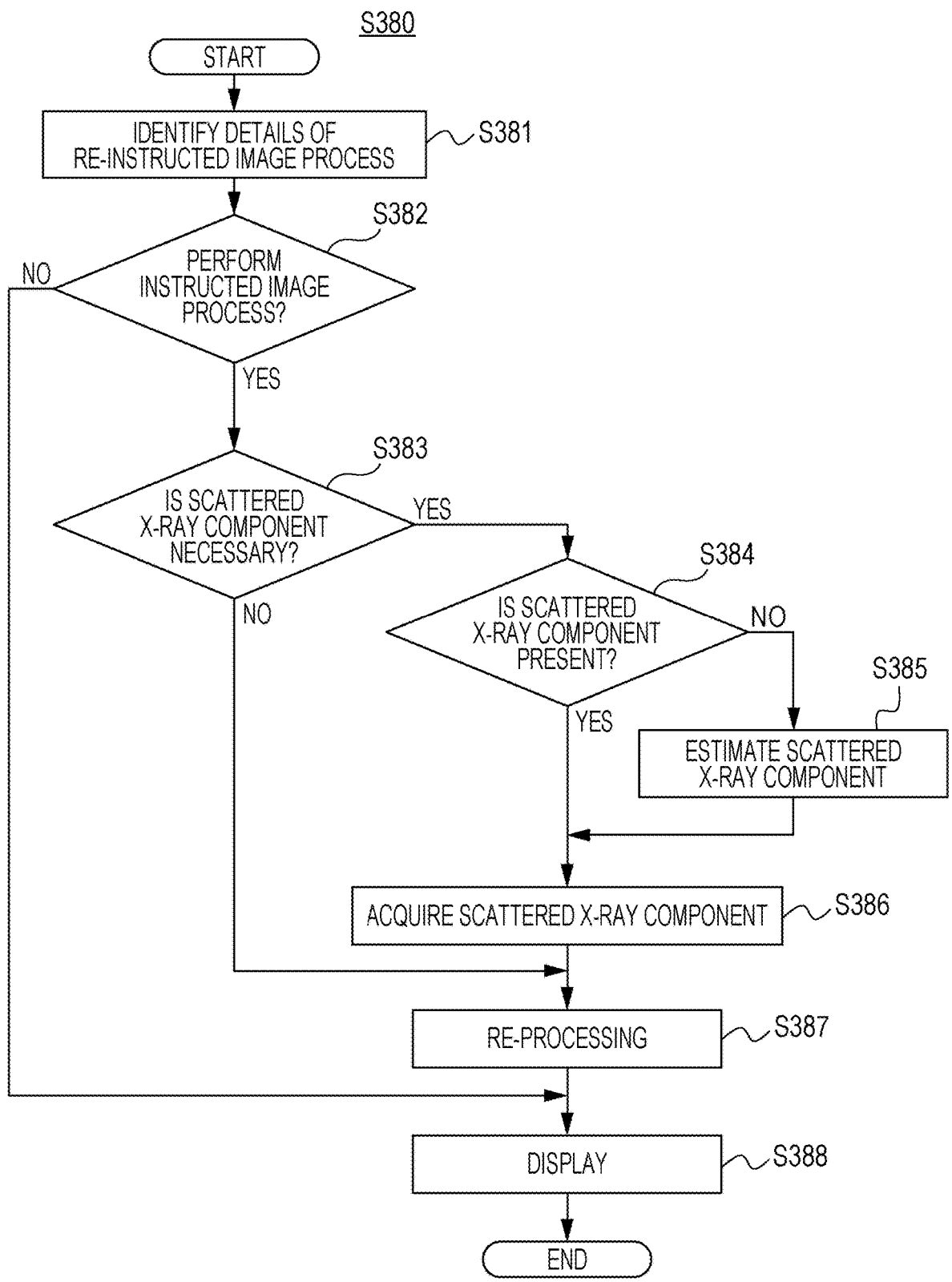
FIG. 4 illustrates a flow for changing an image process according to an embodiment of the present invention.

Next, a flow of an image process to be performed in step S380 in response to an instruction for performing the image process again in step S370 will be described in detail with reference to FIG. 4.

In step S381, details of an instruction for performing an image process again are identified. For example, regarding an instructed image process, a parameter before an instruction input by a user and a parameter after the instruction are obtained. In step S382, based on the identified instruction detail and the user information acquired in step S310, whether the instructed image process is permitted to the user or not is determined. If the instructed process is not permitted, the processing moves to step S388. The display control module 215 displays on the monitor 106 a screen notifying the user of that the process is not permitted to the user. The flow for performing an image process again ends, and the processing moves to step S390. In step S390, the output control module 214 controls so as not to output a new image based on the determination that an image process is not to be performed in step S380. The image processing apparatus 105 returns to the state in which an operation input for ending the examination or an instruction to perform an image process again is acceptable.

If the image process instructed to perform again is permitted to the user, whether the image process requires a scattered X-ray component or not is determined in step S383. An image process not requiring a scattered X-ray component may be an image process as displayed in the region 602, for example. In response to the change if any, the processing moves to step S387 where the image process is performed in response to a user's operation input. In step S387, the display control module 214 displays a re-processed image having undergone the instructed image process in the region 601. A case will be described where an operation input for selecting an "Crop" image process which cuts out a range having an image represented by the icon 602*i* is performed, for example. In step S387, a user may designate a desired range through the operating unit 107, and the image processing module 220 generates a re-processed image acquired by performing cut-out processing on the designated range. In step S388, the display control module 214 displays the re-processed image in the region 601. The flow of the change ends, and the processing moves to step S390. In step S390, the output control module 214 outputs the re-processed image. Here, a change history and a parameter relating to the image process after the change may be saved in the information to be attached to the re-processed image. The same output scheme is applied as that in step S360. The image processing apparatus 105 returns to the state in which an operation input for ending the examination or an instruction to perform an image process again is acceptable.

Next, a case will be described in which the image process instructed to perform again is permitted to the user and it is determined in step S383 that the image process requires a scattered X-ray component. Examples of such an image process requiring a scattered X-ray component may include a change of the degree of reduction of a scattered X-ray component and a change of an image process to be performed based on an image acquired before a scattered X-ray component is reduced. If such a change is instructed as the image process, whether data of a scattered X-ray component estimated and generated in the past based on the image subjecting to the image process have been saved or not with reference to the information attached to the image. For example, if a scattered-ray image ID is stored in a private tag defined in the information attached under DICOM standards, it is determined that the data of the scattered X-ray component have been saved. If the scattered-ray image ID is not stored, it is determined that the data of the scattered X-ray component have not been saved. In another example, an X-ray image captured in the past may be read out from the SSD 206, for example, in step S340. Also if information regarding the image process performed by the image processing module 220 is not attached to the read out X-ray image, it is determined that the data of the scattered X-ray component have not been saved. If the data of the scattered X-ray component have been saved, the processing moves to step S386 where the scattered X-ray component is acquired. The scattered X-ray component is read out from the SSD 206 or the PACS 114 based on the scattered-ray image ID. A case will be described in which an operation input for changing is given in the region 610 displaying a detail of the scattered ray reduction process, for example. It is assumed that a user changes a grid name displayed in the region 612 to change the primary X-ray transmittance and the scattered X-ray transmittance to be referred in the scattered-ray component reduction process. Based on the scattered X-ray component S acquired in step S386, an image process for changing the degree of reduction of the scattered X-ray component is performed in step S374. The resulting re-processed image M" may be expressed by Expression (4).

$$M''=\alpha'P+\beta'S \quad (4)$$

where $\alpha'$ is a primary X-ray transmittance after the change and $\beta'$ is a scattered X-ray transmittance after the change.

In step S388, the display control module 215 displays the re-processed image M" in the region 601. The flow of the change ends, and the processing moves to step S390. In step S390, when the output control module 214 is output a file of the re-processed image, a change history and a parameter relating to the image process after the change may be saved in the information to be attached to the re-processed image. The image processing apparatus 105 returns to the state in which an operation input for ending the examination in step S3100 or an instruction to perform an image process again in step S370 is acceptable.

In a case where the image process instructed to perform again is permitted to the user, it is determined that the image process requires a scattered X-ray component and it is determined in step S384 that data of the scattered X-ray component have not been saved, the processing moves to step S385 where a process for estimating a scattered X-ray component is performed. For example, there may be a case in which the process for reducing a scattered X-ray component is not performed in step S350 on the image acquired in step S340 but is performed later. In this case, the process for estimating a scattered X-ray component is performed in step S385 based on an image subjecting to the instructed image process. With reference to the information attached to the image subjecting to the instructed image process, an image corresponding to the image 355 is acquired if possible. Then, a scattered X-ray component is estimated based on the acquired image. If it is not possible to acquire such an image, a scattered X-ray component is estimated based on the image subjecting to the change. In step S386, the scattered X-ray component estimated in step S385 is acquired. In step S387, a process is performed for reducing the scattered X-ray component to a degree desired by a user. In step S388, the display control module 215 display s the re-processed image acquired in step S387 in the region 601. The flow of the image process ends in response to the corresponding instruction, and the processing moves to step S390. In step S390, information by which the scattered X-ray component estimated in step S385 can be identified, such as the scattered-ray image ID is attached to the re-processed image for output. The same output scheme is applied as that in step S360. The image processing apparatus 105 returns to the state in which an operation input for ending the examination or an instruction to perform an image process again is acceptable.

According to this embodiment, a scattered-ray image ID is given as identification information for identifying the scattered X-ray component 356, and the ID is saved in association with the processed image 358. However, any kind of information may be associated if the scattered X-ray component 356 can be acquired based on the information. For example, instead of a scattered-ray image ID, a path indicating a storage location in the SSD 206 or PACS 114 storing the scattered X-ray component 356 may be handled as the identification information. In other example, in step S360 or step S380, the output control module 214 does not output the scattered X-ray component 356. In this case, identification information for associating the X-ray image acquired in step S340 and the processed image 358 is attached to the processed image 358 in advance. Thus, the processed image 358 is subtracted from the X-ray image to acquire the scattered X-ray component as required.

Figure 3A:
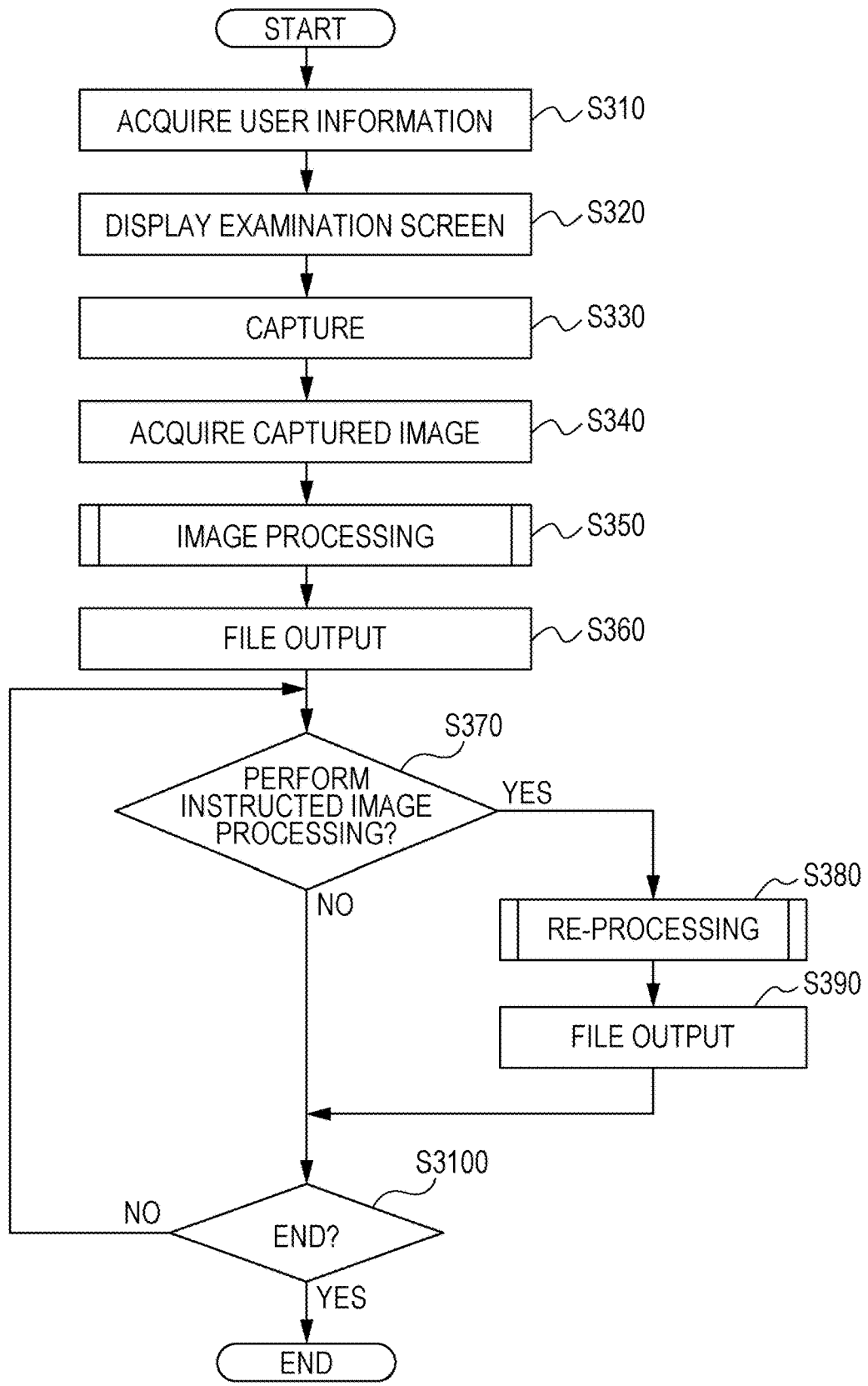
Figure 3B:
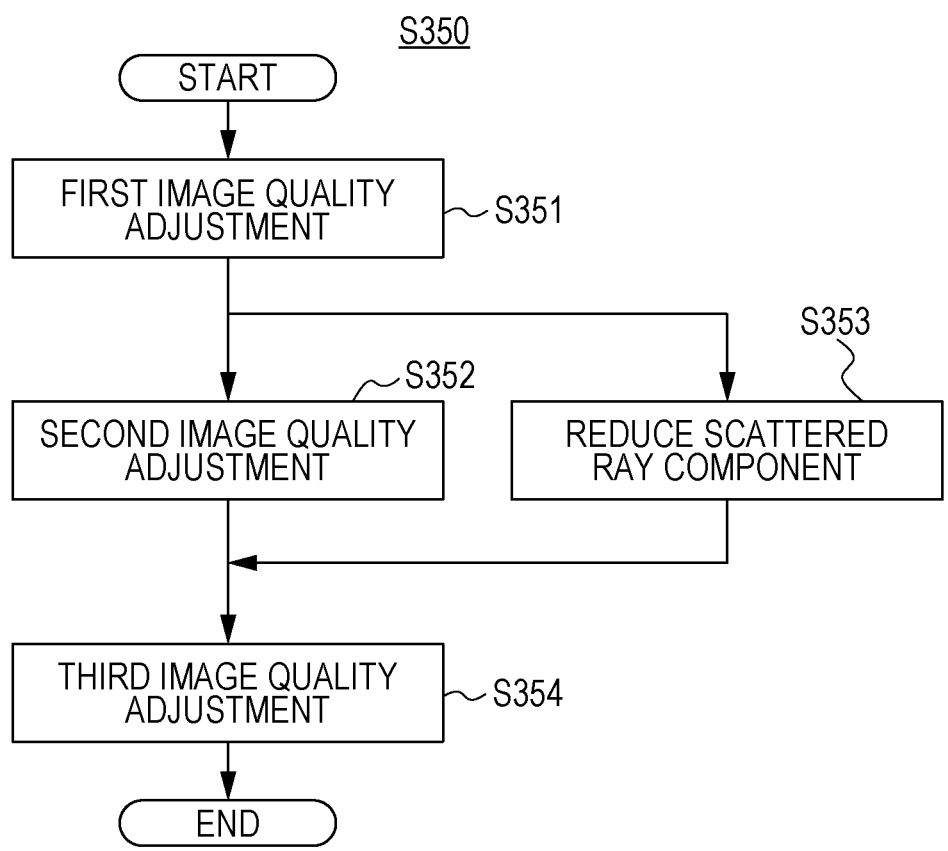

According to this embodiment, after the processing in the steps illustrated in FIG. 3A ends, the state is obtained in which an operation input for ending the examination is acceptable. However, such an operation input for ending the examination may be given at any time point. In a case where an operation input for ending an examination is received in the middle of the processing, the display control module 214 displays on the monitor 106 a screen notifying a user of that the processing is halfway. When the examination is finished in the middle of the processing, an image displayed in the region 601 is output to the SSD 206 when the operation input is received, and information describing the processing performed before the operation input is received is attached to the image which is then saved.

According to this embodiment, the degree of reduction of a scattered X-ray component is changed, for example. However, a limitation for the degree of reduction of a scattered X-ray component may be provided. As a scattered X-ray component decreases, the amount of the signal component decreases. Providing a limitation on the degree of reduction can prevent excessive reduction of a scattered X-ray component which reduces image quality more. Such a limitation on the degree of reduction may be set in advance for each facility. Such a limitation may also be set in accordance with a condition such as an imaging object region. For example, for a region where a radiation scatters a little such as a hand, the scattered-ray reduction process may be set to be disabled. For a region where a radiation can scatter more easily such as the chest, the scattered-ray reduction process may be set to be performed to a degree by which a user can observe it easily. For a region where a radiation can scatter much more easily such as the abdomen than the chest and a less primary X-ray component can thus be generated, the degree of reduction may be set to lower. The set value for limiting the degree of reduction may be permitted to be changed by an authorized user only. A user who is permitted to change the set value for a limitation on the degree of reduction, which is determined with reference to the user information acquired by the imaging control module 211, can change the set value. To a user who is not permitted to change the set value for a limitation on the degree of reduction, a screen notifying a user of that the change is not permitted is displayed on the monitor 106 under control of the display control module 215.

Having described that, according to this embodiment, an image process as illustrated in the region 602 is performed or a detail of the scattered-ray reduction process is performed as an example of an image process to be performed again, the present invention is not limited thereto. For example, settings of imaging conditions for an X-ray image may be changed after an imaging operation. More specifically, when an X-ray image is captured in step S330, an improper imaging condition may possibly be applied. In a case where an imaging condition for X-ray imaging of the abdomen is improperly applied for X-ray imaging for the chest, the parameter to be used for an image process in step S350 is a parameter suitable for an X-ray imaging of the abdomen. A scattered X-ray component is then estimated, and the scattered X-ray component is output in association with the processed image or X-ray image in step S360. When a user instructs to perform imaging again by changing the imaging conditions to those for the chest, the changed conditions are identified in step S381. If it is determined in step S382 that the image process is permitted to the user and if it is determined in step S383 that the image process requires a scattered X-ray component, the processing moves to step S384. In step S384, whether the scattered X-ray component has been output in an image process in the past or not is determined. The information attached to the image subjecting to the instructed image process includes information for identifying the scattered X-ray component output in step S360. However, even though the scattered X-ray component is output, if the captured region is different, a scattered X-ray component is estimated by a scheme for the region again. A process for estimating a scattered X-ray component is performed by a scheme for the chest in step S385, and the scattered X-ray component is acquired in step S386. An image process including a process for reducing the scattered X-ray component acquired in step S386 is performed in step S387. In step S388, a re-processed image reflecting the change is displayed on the monitor 106 under control of the display control module 215. In step S390, the output control module 214 attaches a scattered-ray image ID for identifying the scattered X-ray component estimated in step S385 to the re-processed image for output. The output control module 214 outputs data regarding the scattered X-ray component estimated in step S385 to a non-volatile memory such as the SSD 206. The data regarding the scattered X-ray component generated under the improper imaging conditions and the scattered-ray image ID for identifying it may be deleted. Thus, the change suitable for the imaging conditions can be performed.

Having described that, according to this embodiment, the same scheme is used before and after the change of the scattered ray reduction process, for example, the present invention is not limited thereto. For example, it may correspond to a case where an X-ray image captured in the past (hereinafter, called a past image) is changed. A detail of a change of an image process to be performed on the past image is identified in step S381. The change is assumed, for example, as an image process for changing the degree of reduction of a scattered X-ray component. In step S382, whether the instructed image process is permitted to a user or not is determined. If the user is permitted, the processing moves to step S383. the instructed image process is determined as an image process requiring a scattered X-ray component because it is a process for changing the degree of reduction of a scattered X-ray component. The processing then moves to step S384 where whether data of a scattered X-ray component have been output in the past or not is determined. In other words, whether a scattered X-ray component has been estimated and output in the past or not is determined based on the identification information attached to the past image. In this case, as the information for identifying the output scattered X-ray component, information for identifying a scheme used for the estimation, that is, the estimation algorithm is also referred. The information describing the scheme used for the estimation may be version information of the corresponding software program. In step S381, a scheme used by the scattered-ray estimating module 221 when an instruction to perform an image process again is received and a scheme described by the identification information attached to the past image are referred. If these schemes are different, the display control module 215 displays on the monitor 106 a screen notifying the user of that the estimation algorithm is different. The user can select whether the change is performed based on the scattered X-ray component output in the past or a scattered X-ray component is to be estimated and be output again by applying the currently used estimation algorithm. The scattered ray reduction process may be performed based on the scattered X-ray component estimated by applying the same estimation algorithm as that of the currently used one so that the past image and the current X-ray image can be compared more precisely.

According to this embodiment, it may be controlled so as to disable a function not permitted to a user or inhibit execution of an image process instructed by the user. These controls may be implemented by the imaging control module 211 and display control module 215. For example, the display control module 215 may control so as not to display on the monitor 106 a region relating to a process not permitted to the user based on the user information acquired by the imaging control module 211 among regions for performing operation inputs for processes as illustrated in FIGS. 6A and 6B. In another example, the display control module 215 may control so as to display on the monitor 106 the region relating to a process not permitted to the user but deny an operation input. In another example, the display control module 215 may display on the monitor 106 a region relating to a process not permitted to the user and, if an operation input therefor is given, display on the monitor 106 a screen notifying the user of that the process is not permitted. As another example, a control will be described which is to be performed in a case where a limitation is defined on the degree of reduction of a scattered X-ray component as described above. The region 612 or region 613 in FIGS. 6A and 6B corresponds to the region on which an operation input for setting a detail of the degree of reduction. In a case where it is set to inhibit reduction to a degree indicated by a certain value or more, the display control module 214 controls so as to inhibit input of a value higher than the value. For example, on the number line displayed in the region 613, the icon indicative of the position on the number line displayed on the monitor 106 is controlled so as to be operated to values higher than the certain value.

The present invention may be implemented by processing including supplying a program which implements one or more functions of the aforementioned embodiments to a system or an apparatus over a network or through a storage medium and reading and executing the program by one or more processors in a computer of the system or apparatus. The present invention may also be implemented by a circuit (such as an ASIC) which implements the one or more functions.

The image processing apparatus according to the aforementioned embodiment is a single apparatus. However, the present invention also includes an embodiment in which the aforementioned processing is executed in an image processing system in which a plurality of apparatuses including the information processing apparatus are combined mutually communicably. Alternatively, the aforementioned processing may be executed by a server apparatus or server group common to a plurality of modalities. In this case, the common server apparatus corresponds to the image processing apparatus according to an embodiment, and the server group corresponds to an image processing system according to an embodiment. A plurality of apparatuses included in the information system 120 or the image processing system may only be required to be capable of communication at a predetermined communication rate and may not be required to be present within one facility or within one country.

Embodiments of the present invention may include an embodiment in which a software program implementing functionality of any one of the aforementioned embodiments may be supplied to a system or an apparatus, and a computer in the system or the apparatus may read out and execute code of the supplied program.

Therefore, the program code installed in a computer for causing the computer to execute the processing according to this embodiment is also an embodiment of the present invention. Based on an instruction included in a program read out by such a computer, an OS running on the computer may execute a part or all of actual processing so that the processing can implement the functionality of any one of the aforementioned embodiments.

Combinations of the aforementioned embodiments may also be included in embodiments of the present invention.

Thus, because performing an image process on a radiographic image again may not require a process for reducing a scattered-ray component again, the time required for the processing can be reduced.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-132178, filed Jun. 30, 2015, which is hereby incorporated by reference herein in its entirety.

What is claimed is:

1. An image processing apparatus to reduce a scattered-ray component from a radiographic image containing the scattered-ray component, the image processing apparatus comprising:
   a memory storing a program;
   one or more processors configured to execute the program;
   an acquiring unit configured to acquire a radiographic image using a radiation detector that detects a radiation through an object;
   a scattered-ray estimating unit configured to estimate an estimated scattered-ray component contained in the radiographic image, wherein the scattered-ray component contained in the radiographic image originates from a scattered ray which is a radiation scattered in the object;
   a scattered-ray reducing unit configured to reduce the contained scattered-ray component from the radiographic image;
   an output unit configured to output data of a scattered-ray component;

an identifying unit configured to attach, to the radiographic image, identification information for identifying the contained scattered-ray component; and a control unit configured to control whether data, output by the output unit, of a scattered-ray component is to be used based on a detail of an instruction to perform an image process and the identification information in a case where the instruction is received again, wherein, in a case where a reduction process performed by the scattered-ray reducing unit for reducing the contained scattered-ray component corresponding to the identification information is the same as a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, wherein, in a case where the instruction indicates performing an image process using data of a scattered-ray component and the data identification information is not attached to one of the radiographic image and the processed image, the control unit is configured to control the scattered-ray reducing unit to estimate a scattered-ray component contained in the radiographic image, and wherein the acquiring unit, the scattered-ray estimating unit, the scattered-ray reducing unit, and the identifying unit are implemented by the one or more processors.

2. The image processing apparatus according to claim 1, wherein the identification information includes at least one of information for acquiring the estimated scattered-ray component from a storage and information for identifying a procedure for estimating the contained scattered-ray component.

3. The image processing apparatus according to claim 1, wherein, in a case where the instruction indicates performing an image process using data of a scattered-ray component and data of a scattered-ray component output from the output unit can be acquired from the storage based on the identification information, the control unit is configured to control to acquire data from the storage and to control to use a data of a scattered-ray component output from the output unit in the instructed image process.

4. The image processing apparatus according to claim 1, wherein the output unit is configured to output data of a scattered-ray component estimated by the scattered-ray reducing unit in the instructed image process.

5. The image processing apparatus according to claim 1, wherein the identifying unit is configured to attach, in the instructed image process, identification information for identifying data of the scattered-ray component estimated by the scattered-ray reducing unit to at least one of the radiographic image or an image having undergone the instructed image process.

6. The image processing apparatus according to claim 1, wherein, in a case where, as a procedure for estimating a scattered-ray component, a procedure described in the identification information and a procedure to be performed by the scattered-ray reducing unit when an instruction indicating an image process on the radiographic image is received again are different, the control unit is configured to control the scattered-ray reducing unit to newly estimate a scattered-ray component contained in the radiographic image without using data of a scattered-ray component acquired based on the identification information.

7. The image processing apparatus according to claim 1, further comprising an adjusting unit implemented by the one or more processors and configured to adjust a degree of reduction of the contained scattered-ray component.

8. A method for an image processing apparatus to reduce a scattered-ray component from a radiographic image containing the scattered-ray component, the method comprising:

acquiring, by an acquiring unit, a radiographic image using a radiation detector that detects a radiation through an object;

estimating, by a scattered-ray estimating unit, an estimated scattered-ray component contained in the radiographic image, wherein the scattered-ray component contained in the radiographic image originates from a scattered ray which is a radiation scattered in the object;

reducing, by a scattered-ray reducing unit, the contained scattered-ray component from the radiographic image;

outputting, by an output unit, data of a scattered-ray component;

attaching, by an identifying unit and to the radiographic image, identification information for identifying the contained scattered-ray component; and controlling whether data, output by the output unit, of a scattered-ray component is to be used based on a detail of an instruction to perform an image process and the identification information in a case where the instruction is received again, wherein, in a case where a reduction process performed by the scattered-ray reducing unit for reducing the contained scattered-ray component corresponding to the identification information is the same as a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, and wherein, in a case where the instruction indicates performing an image process using data of a scattered-ray component and the data identification information is not attached to one of the radiographic image and the processed image, controlling includes controlling the scattered-ray reducing unit to estimate a scattered-ray component contained in the radiographic image.

9. A non-transitory computer-readable storage medium storing a program to cause an image processing apparatus to perform a method to reduce a scattered-ray component from a radiographic image containing the scattered-ray component, the method comprising:

acquiring, by an acquiring unit, a radiographic image using a radiation detector that detects a radiation through an object;

estimating, by a scattered-ray estimating unit, an estimated scattered-ray component contained in the radiographic image, wherein the scattered-ray component contained in the radiographic image originates from a scattered ray which is a radiation scattered in the object;

reducing, by a scattered-ray reducing unit, the contained scattered-ray component from the radiographic image;

outputting, by an output unit, data of a scattered-ray component;

attaching, by an identifying unit and to the radiographic image, identification information for identifying the contained scattered-ray component; and controlling whether data, output by the output unit, of a scattered-ray component is to be used based on a detail of an instruction to perform an image process and the identification information in a case where the instruction is received again, wherein, in a case where a reduction process performed by the scattered-ray reducing unit for reducing the contained scattered-ray component corresponding to the identification information is the same as a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, and wherein, in a case where the instruction indicates performing an image process using data of a scattered-ray component and the data identification information is not attached to one of the radiographic image and the processed image, controlling includes controlling the scattered-ray reducing unit to estimate a scattered-ray component contained in the radiographic image.

10. An image processing apparatus to reduce a scattered-ray component from a radiographic image containing the scattered-ray component, the image processing apparatus comprising:

a memory storing a program;

one or more processors configured to execute the program;

an acquiring unit configured to acquire a radiographic image using a radiation detector that detects a radiation through an object;

a scattered-ray estimating unit configured to estimate an estimated scattered-ray component contained in the radiographic image, wherein the scattered-ray component contained in the radiographic image originates from a scattered ray which is a radiation scattered in the object;

a scattered-ray reducing unit configured to reduce the contained scattered-ray component from the radiographic image;

an output unit configured to output data of a scattered-ray component;

an identifying unit configured to attach-, to the radiographic image, identification information for identifying the contained scattered-ray component; and a control unit configured to control whether data, output by the output unit, of a scattered-ray component is to be used based on a detail of an instruction to perform an image process and the identification information in a case where the instruction is received again, wherein, in a case where the contained scattered-ray component corresponding to the identification information exists in a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, wherein, in a case where the instruction indicates performing an image process using data of a scattered-ray component and the data identification information is not attached to one of the radiographic image and the processed image, the control unit is configured to control the scattered-ray reducing unit to estimate a scattered-ray component contained in the radiographic image, and wherein the acquiring unit, the scattered-ray estimating unit, the scattered-ray reducing unit, and the identifying unit are implemented by the one or more processors.

11. A method for an image processing apparatus to reduce a scattered-ray component from a radiographic image containing the scattered-ray component, the method comprising:

acquiring, by an acquiring unit, a radiographic image using a radiation detector that detects a radiation through an object;

estimating, by a scattered-ray estimating unit, an estimated scattered-ray component contained in the radiographic image, wherein the scattered-ray component contained in the radiographic image originates from a scattered ray which is a radiation scattered in the object;

reducing, by a scattered-ray reducing unit, the contained scattered-ray component from the radiographic image;

outputting, by an output unit, data of a scattered-ray component;

attaching, by an identifying unit and to the radiographic image, identification information for identifying the contained scattered-ray component; and controlling whether data, output by the output unit, of a scattered-ray component is to be used based on a detail of an instruction to perform an image process and the identification information in a case where the instruction is received again, wherein, in a case where the contained scattered-ray component corresponding to the identification information exists in a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, and wherein, in a case where the instruction indicates performing an image process using data of a scattered-ray component and the data identification information is not attached to one of the radiographic image and the processed image, controlling includes controlling the scattered-ray reducing unit to estimate a scattered-ray component contained in the radiographic image.

12. A non-transitory computer-readable storage medium storing a program to cause an image processing apparatus to perform a method to reduce a scattered-ray component from a radiographic image containing the scattered-ray component, the method comprising:

acquiring, by an acquiring unit, a radiographic image using a radiation detector that detects a radiation through an object;

estimating, by a scattered-ray estimating unit, an estimated scattered-ray component contained in the radiographic image, wherein the scattered-ray component contained in the radiographic image originates from a scattered ray which is a radiation scattered in the object;

reducing, by a scattered-ray reducing unit, the contained scattered-ray component from the radiographic image;

outputting, by an output unit, data of a scattered-ray component;

attaching, by an identifying unit and to the radiographic image, identification information for identifying the contained scattered-ray component; and controlling whether data, output by the output unit, of a scattered-ray component is to be used based on a detail of an instruction to perform an image process and the identification information in a case where the instruction is received again, wherein, in a case where the contained scattered-ray component corresponding to the identification information exists in a reduction process performed by the scattered-ray reducing unit for reducing the contained scattered-ray component from a radiographic image newly acquired by the acquiring unit, the scattered-ray reducing unit reduces the contained scattered-ray component from the radiographic image newly acquired by the acquiring unit using the contained scattered-ray component corresponding to the identification information, wherein the identifying unit further is configured to attach data identification information to at least one of the radiographic image and a processed image acquired by performing an image process thereon by the scattered-ray reducing unit, wherein the data identification information is for identifying data, output by the output unit, of a scattered-ray component, and wherein, in a case where the instruction indicates performing an image process using data of a scattered-ray component and the data identification information is not attached to one of the radiographic image and the processed image, controlling includes controlling the scattered-ray reducing unit to estimate a scattered-ray component contained in the radiographic image.

* * * * *